United States Patent [19]

Evers et al.

[11] 4,181,681

[45] Jan. 1, 1980

[54] 2-AMINO-4-ETHYNYLPHENOL

[75] Inventors: Robert C. Evers; George J. Moore, both of Dayton, Ohio

[73] Assignee: The United States of America as represented by the Secretary of the Air Force, Washington, D.C.

[21] Appl. No.: 925,899

[22] Filed: Jul. 19, 1978

[51] Int. Cl.$^2$ ............................................. C07C 91/44
[52] U.S. Cl. ..................................... 260/575; 528/210
[58] Field of Search ...................... 260/575, 578, 571; 528/210

[56] References Cited

U.S. PATENT DOCUMENTS

| 3,700,743 | 10/1972 | Relles | 260/668 R |
|---|---|---|---|
| 3,928,450 | 12/1975 | Bilow et al. | 260/571 |
| 3,981,932 | 9/1976 | Diamond | 260/578 X |

OTHER PUBLICATIONS

Morrison et al., "Organic Chemistry", 3rd edition, pp. 673 & 677 (1975).
Fieser et al., "Reagents for Organic Synthesis", vol. 1, pp. 441 & 1081 (1967).
Schofield et al., "Chemical Abstracts", vol. 44, Ab. No. 2992g (1950).
Cook et al., "Chemical Abstracts", vol. 58, Ab. No. 12390d (1963).

*Primary Examiner*—John Doll
*Attorney, Agent, or Firm*—Joseph E. Rusz; Cedric H. Kuhn

[57] ABSTRACT

2-Amino-4-ethynylphenol, a novel compound, is prepared by a four-step synthetic sequence in which the key reaction is the treatment of 4-acetoxy-3-nitroacetophenone with a Vilsmeier reagent derived from N,N-dimethylformamide and phosphorus oxychloride. The compound is useful as an endcapping agent in the synthesis of fluorocarbon ether bibenzoxazole oligomers which, because of the presence of acetylenic terminal groups, can be cured by thermal means to provide broad-use temperature, fuel and fluid resistant vulcanizates.

2 Claims, No Drawings

2-AMINO-4-ETHYNYLPHENOL

RIGHTS OF THE GOVERNMENT

The invention described herein may be manufactured and used by or for the Government of the United States for all governmental purposes without the payment of any royalty.

FIELD OF THE INVENTION

This invention relates to 2-amino-4-ethynylphenol. In one respect it relates to a process for synthesizing the compound.

BACKGROUND OF THE INVENTION

Extensive research work has been performed with the object of providing thermally stable, elastomeric polymers for various aerospace seal and sealant applications. To meet the rigid requirements for such applications, a polymer must also retain its elastomeric properties at sub-zero temperatures. Polymers that advance the art in meeting the requirements are disclosed by one of us, namely, Robert C. Evers, in U.S. Pat. Nos. 3,846,376; 3,994,861 and 4,064,109.

In the above-mentioned patents, fluorocarbon ether bibenzoxazole polymers are disclosed that possess a combination of high thermooxidative stability and low glass transition temperatures. In order to exhibit elastomeric properties, these moderate to high molecular weight bibenzoxazole polymers must be cured. The preferred method of cure is a magnesium oxide-benzoyl peroxide catalyzed cure through aliphatic or olefinic cure sites incorporated within the backbone of the polymer chain. During curing of the polymers, volatiles are evolved with the result that voids may form in the cured product. Thus, there is a need for fluorocarbon ether bibenzoxazole oligomers that can be cured without the evolution of volatiles to an elastomer exhibiting high thermooxidative stability and low temperature flexibility.

It is a principal object of this invention to provide an endcapping agent which can be used in providing fluorocarbon ether bibenzoxazole oligomers with acetylenic terminal groups which make possible a volatile-free cure of the oligomers to vulcanizates possessing a combination of high thermooxidative stability and low glass transition temperatures.

Another object of the invention is to provide a process for synthesizing 2-amino-4-ethynylphenol.

Other objects and advantages of the invention will become apparent to those skilled in the art upon consideration of the accompanying disclosure.

SUMMARY OF THE INVENTION

The present invention resides in an acetylenic o-aminophenol, namely, 2-amino-4-ethynylphenol. The compound has the following structural formula:

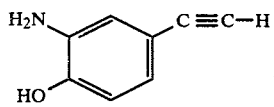

In one embodiment, the invention lies in a four-step process for synthesizing 2-amino-4-ethynylphenol. The steps involved in the process can be illustrated by the following equations:

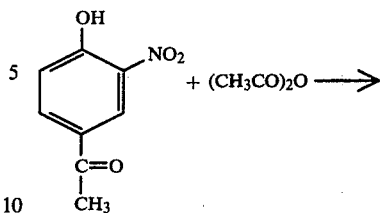

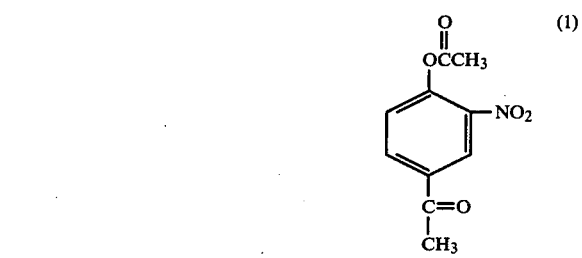

(1)

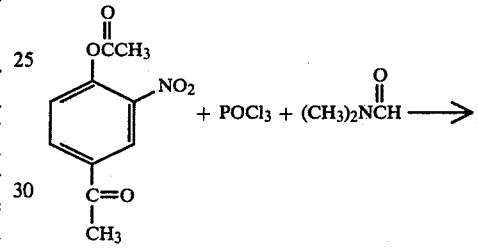

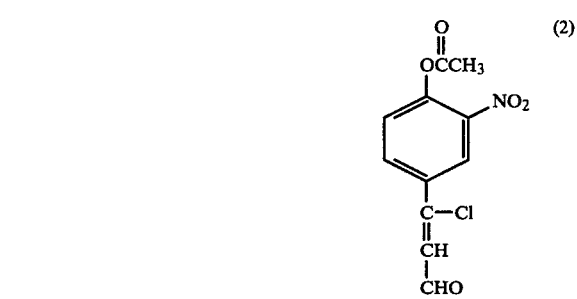

(2)

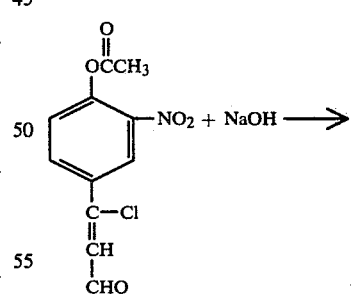

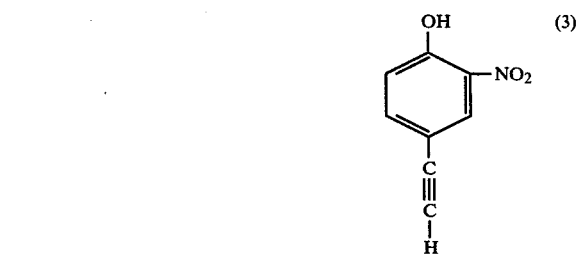

(3)

-continued

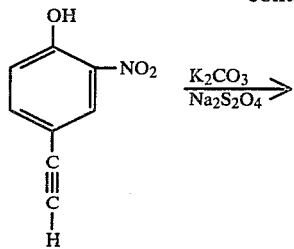

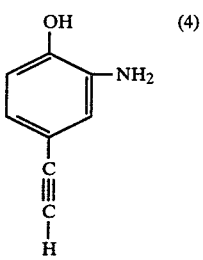

In performing the foregoing reactions, initially, as shown by equation (1), a mixture of 4-hydroxy-3-nitroacetophenone and acetic anhydride is heated under reflux conditions for a period of about 30 to 60 minutes. During the reaction that occurs the acetic anhydride advantageously functions both as a reactant and a solvent. It is usually preferred, therefore, to use an excess of the acetic anhydride, e.g., about 1 to 10 moles of anhydride per mole of 4-hydroxy-3-nitroacetophenone. At the end of the reaction period, excess acetic anhydride is stripped off under reduced pressure, leaving a solid product. The product is purified by recrystallization from a non-solvent, such as isopropanol, to yield crystals of 4-acetoxy-3-nitroacetophenone.

In the second step (equation 2), phosphorus oxychloride is added to N,N-dimethylformamide to form a solution containing a Vilsmeier reagent. In forming the reagent, a molar excess of N,N-dimethylformamide is usually employed, e.g., 2 to 5 moles of N,N-dimethylformamide per mole of phosphorus oxychloride. The 4-acetoxy-3-nitroacetophenone prepared in step (1) is then added to the solution at room temperature. The amount of the compound added to the solution can vary with rather broad limits, but to ensure complete reaction it is preferably such that there is a molar excess of the materials forming the Vilsmeier reagent. The reaction temperature is maintained at about 50° to 65° C. for about 2 to 4 hours after which the reaction mixture is poured into ice water. The resultant solution is neutralized with sodium bicarbonate and the precipitate formed is separated by filtration. The crude product is then purified to obtain crystals of 4-acetoxy-3-nitro-$\beta$-chlorocinnamaldehyde.

In the third step of the process (equation 3), 4-acetoxy-3-nitro-$\beta$-chlorocinnamaldehyde is added to a solution of sodium hydroxide. The reaction mixture is maintained at 50° to 80° C. for about 15 to 30 minutes and then cooled at 0° C. In the reaction that occurs, the ester group is hydrolyzed, and hydrogen chloride and carbon monoxide are simultaneously eliminated. The mole ratio of sodium hydroxide to 4-acetoxy-3-nitro-$\beta$-chlorocinnamaldehyde is usually about 3 to 10:1. The cooled solution is neutralized with glacial acetic acid to give a precipitate which is separated by filtration. The precipitate is then purified to give crystals of 4-ethynyl-2-nitrophenol.

In the fourth and final step (equation 4), 4-ethynyl-2-nitrophenol is dissolved in a solution of potassium carbonate. Soodium dithionite is then added and the solution is stirred at room temperature for about 1 to 3 hours. The potassium carbonate acts as a solubilizing agent while the sodium dithionite functions as a reducing agent. A molar excess of each of these compounds as compared to the 4-ethynyl-2-nitrophenol is generally used. The aqueous solution is extracted with methylene chloride after which the product 2-amino-4-ethynylphenol is crystallized from solution by addition of a non-solvent, such as hexane.

As mentioned previously, the acetylenic compound of this invention is useful as an endcapping agent in the synthesis of fluorocarbon ether bibenzoxazole oligomers. Since the compound contains an o-aminophenol structure which is reactive to fluorocarbon ether imidate esters, it can be used to synthesize such oligomers with acetylenic terminal groups. The acetylenic groups are susceptible to thermally-induced addition reactions, thereby making possible a volatile-free cure of the oligomers to rubbery vulcanizates via a combination of chain extension and crosslinking reactions. The preparation of such fluorocarbon ether bibenzoxazole oligomers is described in detail in commonly assigned copending U.S. Patent application Ser. No. (925,900) filed on July 19, 1978, the disclosure of which is incorporated herein by reference.

A more comprehensive understanding of the invention can be obtained by referring to the following illustrative examples which are not intended, however, to be unduly limitative of the invention.

EXAMPLE I

1. Preparation of 4-Acetoxy-3-nitroacetophenone

A mixture of 4-hydroxy-3-nitroacetophenone (50.0 g, 0.28 mole) and acetic anhydride (100.0 g, 0.98 mole) was stirred at reflux for 45 minutes to form a clear, light yellow solution. The excess acetic anhydride was stripped off under reduced pressure to give an oil which gradually solidified. Recrystallization from 500 ml of isopropanol (charcoal) yielded 43.0 g (69% yield) of light yellow crystals of 4-acetoxy-3-nitroacetophenone (m.p. 62°–63° C.).

Analysis: Calc'd: C, 53.80; H, 4.08; N, 6.27; Found: C, 53.54; H, 3,93; N, 6.45.

Molecular weight (mass spectroscopy): Calc'd: 223; Found: 223.

2. Preparation of 4-Acetoxy-3-nitro-$\beta$-chlorocinnamaldehyde

Phosphorus oxychloride (45.0 ml, 0.49 mole) was added dropwise with stirring over a 30 minute period to N,N-dimethylformamide (150 ml, 1.94 mole) (spectral grade) at 20° C. solution had taken on a blood-red color by the time addition was complete, indicating the presence of the Vilsmeier reagent. To the solution at room temperature was added powdered 4-acetoxy-3-nitroacetophenone (43.0 g, 0.19 mole). The reaction temperature was maintained at 55° to 60° C. for three hours at which time the reaction mixture was poured into 1500 ml of ice water. The resultant light tan solution was neutralized with sodium bicarbonate and the precipitate formed was isolated by filtration. It was allowed to air dry on the frit to yield 34 g of crude product which was subsequently dissolved in 400 ml of methylene chloride. The cloudy solution was treated with charcoal, filtered, and an additional 500 ml of methylene chloride along with 500 ml of heptane was added. This solution was treated with charcoal, filtered and reduced in volume to approximately 1700 ml. Upon cooling, an oil separated on the sides of the beaker. The supernatant was decanted, reduced in volume to 1500 ml, and poured into 200 ml of hexane. Yellow crystals separated from the cooled solution to afford 22 g (43% yield) of 4-acetoxy-3-nitro-$\beta$-chlorocinnamaldehyde (m.p. 128°–130° C.).

Analysis: Calc'd: C, 48.98; H, 3.00; N, 5.19; Found: C, 48.96; H, 2.80; N, 5.06.

Molecular Weight (mass spectroscopy): Calc'd: 269; Found: 269.

3. Preparation of 4-Ethynyl-2-nitrophenol

4-Acetoxy-3-nitro-$\beta$-chlorocinnamaldehyde (22.0 g, 0.08 mole) was added to a stirred solution of sodium hydroxide (25 g, 0.63 mole) in 1100 ml of water. The reaction mixture was maintained at 60° to 70° C. for twenty minutes and was then cooled to 0° C. A small amount of insolubles was filtered off and the clear solution was neutralized with glacial acetic acid to give a creamy-white precipitate which was isolated by filtration. After being allowed to air dry on the frit, the crude product was dissolved in 400 ml of methylene chloride. This solution was treated with charcoal, filtered, and reduced in volume to 200 ml to afford, upon cooling, 9.6 g (59% yield) of yellow crystals of 4-ethynyl-2-nitrophenol (m.p. 115°–116° C.).

Analysis: Calc'd: C, 58.92; H, 3.07; N, 8.58; Found: C, 58.85; H, 2.94; N, 8.82.

Molecular Weight (mass spectroscopy): Calc'd: 163; Found: 163.

4. Preparation of 2-Amino-4-ethynylphenol

4-Ethynyl-2-nitrophenol (3.7 g, 0.02 mole) was dissolved in a solution of potassium carbonate (3.7 g, 0.03 mole) in 250 ml of water. Then sodium dithionite (30.0 g, 0.17 mole) was added and the resultant solution stirred at room temperature for one hour. The aqueous solution was extracted repeatedly with methylene chloride (total volume of 1500 ml). The methylene chloride solution was treated with anhydrous magnesium sulfate and then with charcoal. After the filtered solution was reduced in volume to 500 ml, 1500 ml of hexane was added. The resultant solution was reduced in volume to 1200 ml at which time the product began to crystallize out of solution. Cooling to ice water temperature yielded 0.90 g (34% yield) of white crystals of 2-amino-4-ethynylphenol (m.p. >105° C.—vigorous decomposition).

Analysis: Calc'd: C, 72.14; H, 5.33; N, 10.51; Found: C, 72.47; H, 5.66; N, 9.95.

Molecular Weight (mass spectroscopy): Calc'd: 133; Found: 133.

EXAMPLE II

A run was conducted in which a fluorocarbon ether bibenzoxazole oligomer having terminal acetylenic groups was prepared in a condensation reaction represented by the following equation and as described below.

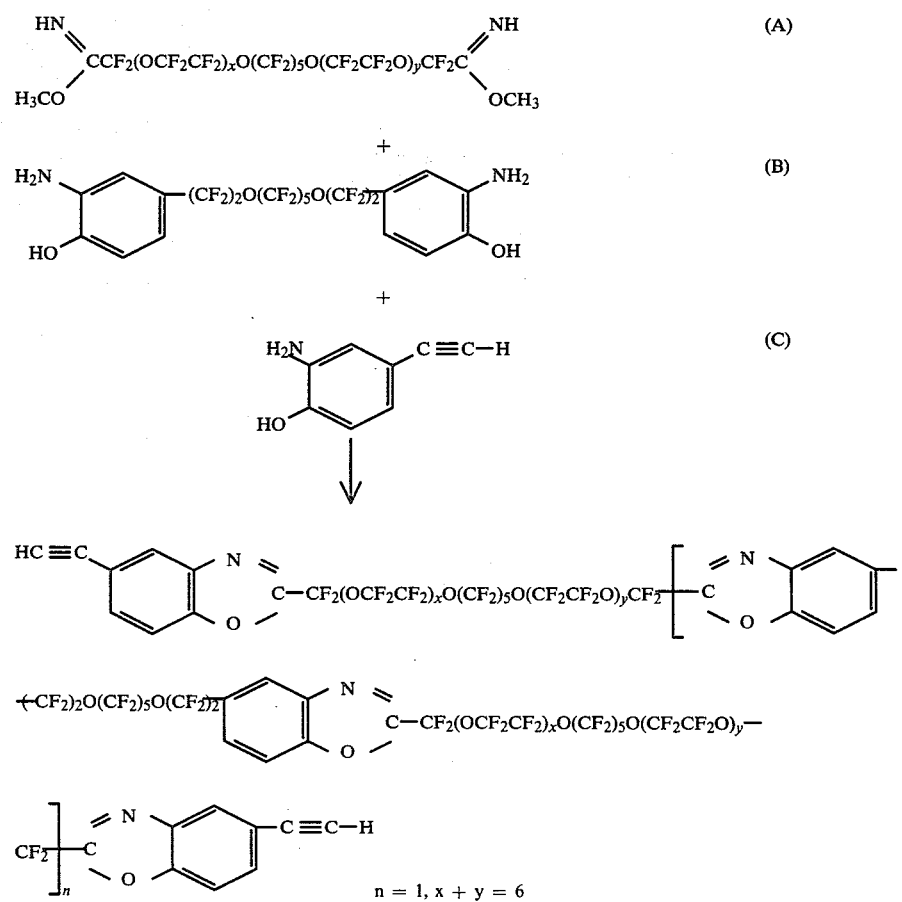

Diimidate ester A (3.586 g, 0.0030 mole) and glacial acetic acid (0.380 g, 0.0063 mole) was dissolved in a mixture of 60 ml of 1,1,2-trichloro-1,2,2-trifluoroethane (Freon 113) and 45 ml of methylene chloride at 45° C. To this clear solution was added bis(o-aminophenol) B (1,048 g, 0.0015 mole) in four portions over the course of an hour. After stirring under nitrogen at 45° C. for 22 hours, the acetylenic compound C (0.445 g, 0.0033 mole) and additional glacial acetic acid (0.380 g, 0.0063 mole) in 15 ml of methylene chloride were added to the clear, pale yellow reaction mixture. The reaction was continued for an additional 20 hours at which time the clear reaction mixture was transferred to a separatory funnel. It was washed successively with water, dilute sodium bicarbonate solution, and again with water. The organic layer was then dried over anhydrous magnesium sulfate, treated with charcoal, and reduced in volume to approximately 15 ml. The clear concentrated solution was transferred to a vial and the remaining organic solvents were carefully removed at 58° C. and 0.01 mm Hg pressure to yield 4.36 g (86% yield) of viscous, pale yellow oligomer.

Analysis: Calc'd: C, 30.05; H, 0.47; N, 1.77; Found: C, 30.20; H, 0.10; N, 1.68.

Infrared spectral analysis confirmed the presence of the terminal acetylene groups and the absence of unreacted o-aminophenol and imidate ester moieties. Differential scanning calorimetry revealed that the oligomer had a glass transition temperature (Tg) of −60° C. Onset of reaction of the terminal acetylenic groups was shown to occur at 195° C. with the maximum rate of reaction being at 280° C. The sample was held in the differential scanning calorimeter at 300° C. for 30 minutes to give a cured, insoluble rubbery product which exhibited a Tg of −46° C.

Approximately one gram of the liquid oligomer was placed in a steel mold and was heated at 160° C. for 16 hours and at 185° C. for twenty-four hours to give a transparent, reddish-brown rubber. Additional heating at 240° C. for three hours did not appear to further advance the cure. The soft, flexible rubber exhibited a Tg of −45° C.

Thermogravimetric analysis in air ($\Delta T=3°$ C./min) revealed onset of weight loss at 350° C. with a 10% weight loss at 475° C. An infrared spectrum (film) of the cured oligomer confirmed the disappearance of the terminal acetylenic groups. The remainder of the infrared spectrum was essentially unchanged. Elemental analysis values of the cured material were almost identical to those of the uncured oligomer.

As seen from the foregoing, use of the compound of this invention in the synthesis of a fluorocarbon either bibenzoxazole oligimer makes it possible to provide the oligomer with acetylenic terminal groups. Because of the presence of these groups, the oligomer can be cured thermally to a rubbery vulcanizate without the undesirable evolution of volatiles. The vulcanizate has a broad use temperature range which renders the material suitable for many aerospace applications such as for seals and sealants.

As will be evident to those skilled in the art, modifications of the present invention can be made in view of the foregoing disclosure without departing from the spirit and scope of the invention.

We claim:
1. 2-Amino-4-ethynylphenol.
2. A process for preparing 2-amino-4-ethynylphenol which comprises the steps of:
  (a) heating a mixture of 4-hydroxy-3-nitroacetophenone and acetic anhydride under reflux conditions for a period of about 30 to 60 minutes, thereby forming 4-acetoxy-3-nitroacetophenone;
  (b) adding 4-acetoxy-3-nitroacetophenone from step (a) to a solution formed by adding phosphorus oxychloride to N,N-dimethylformamide and maintaining the resulting mixture at a temperature ranging from about 50° to 65° C. for about 2 to 4 hours, thereby forming 4-acetoxy-3-nitro-$\beta$-chlorocinnamaldehyde;
  (c) adding 4-actoxy-3-nitro-$\beta$-chlorocinnamaldehyde from step (b) to a solution of sodium hydroxide and maintaining the resulting reaction mixture at a temperature ranging from about 50° to 80° C. for about 15 to 30 minutes, thereby forming 4-ethynyl-2-nitrophenol; and
  (d) dissolving 4-ethynyl-2-nitrophenol from step (c) in a solution of potassium carbonate and then adding sodium dithionite to the solution, thereby forming 2-amino-4-ethynylphenol as the product of the process.

* * * * *